US008273077B2

(12) United States Patent
MacRae et al.

(10) Patent No.: US 8,273,077 B2
(45) Date of Patent: Sep. 25, 2012

(54) SYSTEM AND METHOD FOR TREATING VISION REFRACTIVE ERRORS

(75) Inventors: Scott MacRae, Rochester, NY (US); Manoj Subbaram Venkiteshwar, Rochester, NY (US)

(73) Assignee: University of Rochester, Rochester, NY (US)

( * ) Notice: Subject to any disclaimer, the term of this patent is extended or adjusted under 35 U.S.C. 154(b) by 1649 days.

(21) Appl. No.: 11/403,877

(22) Filed: Apr. 14, 2006

(65) Prior Publication Data

US 2006/0235369 A1    Oct. 19, 2006

Related U.S. Application Data

(60) Provisional application No. 60/671,077, filed on Apr. 14, 2005, provisional application No. 60/725,661, filed on Oct. 13, 2005.

(51) Int. Cl.
*A61B 18/20* (2006.01)

(52) U.S. Cl. .................................. 606/2; 606/3; 606/19

(58) Field of Classification Search .................... 606/2–9
See application file for complete search history.

(56) References Cited

U.S. PATENT DOCUMENTS

| 5,777,719 | A | 7/1998 | Williams et al. |
| 6,508,812 | B1 | 1/2003 | Williams et al. |
| 6,530,917 | B1 * | 3/2003 | Seiler et al. ........................ 606/5 |
| 6,814,729 | B2 | 11/2004 | Youssefi et al. |
| 2004/0054358 | A1 | 3/2004 | Cox et al. |
| 2005/0200809 | A1 * | 9/2005 | Dreher et al. ................. 351/246 |
| 2005/0251115 | A1 | 11/2005 | Cox et al. |
| 2006/0017990 | A1 | 1/2006 | Platt et al. |

FOREIGN PATENT DOCUMENTS

| WO | WO03075778 A1 | 9/2003 |
| WO | WO2004091458 A1 | 10/2004 |

OTHER PUBLICATIONS

Patent Cooperation Treaty, International Search Report, dated Jan. 11, 2007.
G. Schwartz et al., CustomCornea Wavefront Retreatment After Conventional Laser In Situ Keratomileusis, Journal of Cataract & Refractive Surg., Aug. 2005, pp. 1502-1505, vol. 31-Issue 8.
Durrie et al., Alcon LADARWave Customcornea Retreatments, Journal of Retractive Surg., Nov.-Dec. 2005, pp. S804-S807, vol. 21-Issue 6.
MacRae, "University of Rochester Advanced Nomogram," PowerPoint Slide Presentation, Date Unknown, 5 pp.

(Continued)

*Primary Examiner* — Aaron Roane
(74) *Attorney, Agent, or Firm* — Blank Rome LLP (57) ABSTRACT

Disclosed is a computer-implemented method for correcting refractive errors in a living eye using a laser vision correction system that involves first calculating an amount of sphere based on preoperative manifest refraction and higher order aberrations data associated with the eye, and then correcting for the calculated amount of sphere by ablating at least a portion of the eye. The preoperative manifest refraction may include preoperative manifest sphere, preoperative spherical equivalent, regular astigmatism, and oblique astigmatism, and the preoperative higher-order aberrations may include 4th-order spherical and 3rd root mean square. Other factors may also be used to adjust the calculated amount of sphere. A device readable medium for storing the calculation and instructions for operating a laser vision correction system for practicing the method is also disclosed, as is a method of treating refractive errors.

8 Claims, 4 Drawing Sheets

OTHER PUBLICATIONS

Hament, et al., abstract only of "Repeatability and validity of Zywave aberrometer measurements," Journal of Cataract and Refractive Surgery, 2002, vol. 12, pp. 2135-2141, Elsevier, Maryland Heights, MO, USA.

Mirshahi, et al., abstract only of "In vivo and in vitro repeatability of Hartmann-Shack aberrometry," Journal of Cataract and Refractive Surgery, 2003, vol. 12, pp. 2295-2301, Elsevier, Maryland Heights, MO, USA.

* cited by examiner

FIG. 1

(PRIOR ART)

SYSTEM AND METHOD FOR TREATING VISION REFRACTIVE ERRORS

CROSS REFERENCE TO RELATED APPLICATIONS

This application is related to, and claims priority to, U.S. Provisional Patent Application No. 60/671,077, entitled "Strong Vision Method for Enhanced Zyoptix® Outcome," filed on Apr. 14, 2005, and U.S. Provisional Patent Application No. 60/725,661, entitled "Astigmatism Analysis," filed on Oct. 13, 2005, which are expressly incorporated by reference herein.

BACKGROUND OF THE INVENTION

1. Field of Invention

The present invention is generally related to systems and methods for treating refractive errors in human eyes using wavefront-guided or customized laser ablation surgical techniques. In particular, the present invention is related to the use of preoperative manifest refraction information in combination with known preoperative wavefront information to improve the efficacy, or outcome, of using laser ablation techniques, such as LASIK, on human eyes, the efficacy/outcome being measured by postoperative results.

2. Description of the Related Art

One of ordinary skill in the art will understand that myopia refers to a refractive defect of the optical properties of an eye that causes images to focus forward of the retina (i.e., a refractive error). Those optical defects are typically caused by, among other things, defects of the cornea, elongation of the eye structure, other conditions, or a combination of those conditions. Hyperopia, on the other hand, refers a refractive error of the optical properties of an eye that causes images to focus behind the retina. Those optical defects are the result when the optics of the eye are not strong enough for the front to back length of the eye. Astigmatism (or "cylinder," which are used interchangeably) refers to a refractive error that causes light entering the eye to focus on two points rather than one. It is caused by an uneven power of the cornea. Myopia, hyperopia, and astigmatism are the principle refractive errors that cause persons to seek treatment to correct their vision problems.

A manifest refraction analysis is a diagnostic tool used by ophthalmologists whereby a person's refractive error is determined as a means for indicating whether the person would benefit from correction with glasses or contact lenses. As part of that technique, a person looks through a phoropter while the ophthalmologist evaluates each of the person's eyes. A retinal reflex diagnosis technique is often used to assess the magnitude of the refractive error present in the person's eyes. Subjective feedback from the person is used to refine the manifest refraction, which involves the person making choices between image quality as different lenses having different powers are slid into place in the phoropter. At the end of the manifest refraction analysis, a prescription for glasses, contact lenses, and/or refractive surgery may be produced.

It is well known that a wavefront analysis of a person's eyes, using a wavefront sensor like the Zywave® Aberrometer made by Bausch & Lomb, Rochester, N.Y., and pioneered by Dr. David Williams and his team at the University of Rochester, can provide information about the person's visual acuity beyond that which the manifest refraction technique can provide. The wavefront analysis produces a shape of the wavefront of the person's eyes; the shape being described using Zernike polynomials. The polynomial shapes are classified as lower- or higher-order, based on the aberrations of the refracting optics of the eyes. Lower order aberrations, which most people with refractive errors have, consist of the 2nd-order aberration called defocus (i.e., myopia, hyperopia, and astigmatism). Those errors are correctable with glasses, contacts, or interocular lenses. Higher order aberrations, which some people have but in much smaller and varying amounts, consist of the 3rd-, 4th-, 5th-, ..., nth-order aberrations. Higher order aberrations are aberrations of the optics of the eye above and beyond myopia, hyperopia, and astigmatism and they are not typically correctable with glasses or contact lenses.

Several refractive surgery techniques have been developed for correcting the higher order refractive errors in a person's eyes. U.S. Pat. No. 6,814,729 describes a refractive surgery technique using a laser. It teaches that a programmed series of ablating laser pulses are directed onto a patient's eye to reshape the cornea in an attempt to correct a refractive defect of the patient's eye. As noted above, the determination of a particular refractive defect starts with manifest refraction diagnostic information about the patient's eyes and its visual quality. That diagnostic information can be generated by one or more diagnostic devices including wavefront sensors, topography devices, ultrasonic pachymeters, optical coherence tomography (OCT) devices, refractometers, slit lamp ophthalmoscopes (SLOs), iris pattern recognition apparatus, and others that are well known in the art, and by other pertinent information that may be supplied by the surgeon, including surgical environmental conditions, particular patient data, surgeon-specific preferences, and others. According to the above patent, the appropriate input data are then fed to a calculation module in the laser system, which comprises software that uses the input data to determine an appropriate myopia, hyperopia, and astigmatism treatment.

One of the more common laser vision correction techniques is LASIK (i.e., laser-assisted in situ keratomileusis), which is a surgical procedure performed by ophthalmologists using ablation to remove corneal tissue and reshape the optics of the person's eyes. The LASIK laser is guided over the surface being exposed to the laser radiation in accordance with information that was inputted into the computer that operates the laser tracking system. That information is based on, as noted above, the aberrations identified in the person's eyes using a wavefront sensor, such as the Zywave® Aberrometer. Thus, the LASIK surgical procedure is often referred to as "wavefront-guided" laser ablation, and it is often marketed as being "customized" to the person receiving treatment. Customized LASIK has been shown to be effective in treating both the lower order (i.e., sphere and cylinder) and higher order aberrations (i.e., 3rd order and higher).

Other laser ablation surgical techniques are PRK (i.e., photorefractive keratectomy), EpiLASIK, and LASEK (i.e., laser epithelial keratomileusis); however, for purposes of this disclosure, the preferred embodiments of the invention will be described in context with the LASIK procedure.

A more complete technical summary of LASIK surgical procedures is contained in U.S. Patent Application Publication No. 20060017990 as follows: a) a Shack-Hartmann wavefront sensor is used to measure the aberrations in an optical system such as a living eye; b) a nomogram of the light-adjustable cornea's response to irradiation is then consulted to determine the required intensity profile to correct the measured aberrations; c) the required intensity profile is placed on a static mask (e.g. an apodizing filter) or a programmable mask generator (such as a digital mirror device); d) a calibration camera is used in a closed loop operation to correct the digital mirror device to compensate for aberrations in the projection optics and non-uniformity in the light source; e) the cornea is irradiated for the prescribed duration using the appropriate wavelength, intensity, and spatial profile; and f) after a specified diffusion time, the aberrations in the optical system are re-measured to ensure that the proper correction was made. If necessary, the process is repeated until the correction is within an acceptable pre-operative prediction target.

Several studies have reported the safety and efficacy of customized LASIK treatment for myopia. Despite being an advanced technology, it has been found that 24.1-percent of the eyes treated using customized LASIK have postoperative spherical equivalent (SE) of more than ±0.50 diopters (D), and about 10-percent of those eyes require re-treatment (a diopter is a unit of measurement for the power of a lens or of the refractive error measured in an eye). The etiology of postoperative refractive error has been associated with the corneal healing response and laser ablation characteristics.

One LASIK device, the Zyoptix® Custom Ablation system available from Bausch & Lomb, has been in use for several years after completing clinical trials in connection with a U.S. Food & Drug Administration (FDA) premarket approval application (the FDA approved the Zyoptix® system application on Oct. 10, 2003). One of the joint inventors of the present invention led one of the three FDA clinical trial centers involved in the study of the Zyoptix® system. The results of the clinical trials established the efficacy of the Zyoptix® system as follows.

First, 91.5-percent of the trial patients undergoing wavefront-guided laser eye surgery according to the Zyoptix® system had unaided vision of 20/20 or better (i.e., vision without glasses or contacts). Second, 70.3-percent of the trial patients had unaided vision of 20/16 or better. Third, more than 94-percent of the patients maintained or improved from their best-corrected vision with glasses six months post-operatively. Six months after surgery with the Zyoptix® system, 99.0-percent of subjects reported that they were moderately or highly satisfied with their results and 99.7-percent indicated improvement in quality of vision, of which more than 40-percent reported improvement in night vision while driving. None of the patients in the clinical trial reported dissatisfaction with their vision after surgery. Thus, the Zyoptix® system was shown to provide better postoperative refractive outcome than previous vision correction systems.

Despite those impressive results, it was found that the Zyoptix® system, as well as other laser ablation platforms, continued to cause overcorrection of the refractive errors when the system was operated strictly according to the predicted phoropter refraction (PPR) values set by the manufacturer in the programming of the system. Thus, in the case of the Zyoptix® system, the manufacturer determined that the laser output should be reduced by 93-percent to account for that overcorrection (the 93-percent was estimated from a linear regression of the discrepancy between postoperative results and the PPR values). Similarly, in the case of Alcon's LADARVision® system, the manufacture began recommending that the spherical correction be reduced to reduce incidences of overcorrection.

As noted above, the Zyoptix® system, like other systems, contains a set of preprogrammed instructions that may not be suitable for every person undergoing treatment. Surgeons are constantly developing personalized nomograms based upon relevant outcome-influencing factors that they have determined will optimize their treatment outcomes. For example, as described in U.S. Pat. No. 6,814,729, the Zywave® aberrometer, which includes a computer that runs software known in the industry as Zylink® ablation computation software, uses wavefront diagnostic data to determine an appropriate laser shot file for execution by a laser platform such as a Technolas 217Z® laser, also available from Bausch & Lomb. The patent describes a surgeon in Hong Kong that modified the software algorithm by incorporating a customized nomogram that produced optimized myopic correction for Asian patients, and a surgeon in Florida that obtained optimized surgical outcomes using a different myopia treatment nomogram that compensated for humidity effects on outcome. Thus, in addition to output adjustments recommended by the laser manufacturers to reduce incidences of overcorrection (or undercorrection), such as the 93-percent adjustment noted above for the Zyoptix® system, surgeons have been further adjusting their laser outputs and spherical correction calculations to account for various other site-specific factors.

The Kent-Mahon equation took this adjustment technique one step further by accounting for PPR wavefront refraction, sphere and cylinder refraction, but does not use manifest refraction information for sphere and cylinder to adjust the parameters of a laser vision correction systems in order to further refine the treatment and improve the outcome of patients undergoing refractive error surgery.

Similarly, in Bausch & Lomb's U.S. Patent Application Publication No. 20050251115, a method for making a diagnostic measurement to determine lower (second Zernike order or below) and/or higher (third and higher Zernike order) optical aberrations is disclosed in which an adjustment is made to a prospective photorefractive treatment based upon an expected, observed, calculated or otherwise anticipated biodynamical and/or biomechanical effect. Such an effect induces a deviation from an expected result of the prospective treatment in the absence of such biodynamical and/or biomechanical induced deviation. This adjustment, according to the patent application, will advantageously be a calculated or derived adjustment, however, empirical adjustments are entirely suitable as they form a basis for building and/or validating biodynamical and biomechanical models of the eye. That patent application, and other patent disclosures reviewed here to date, do not teach using the nomogram of the present invention.

In fact, to date, neither the Zyoptix® system nor previous known nomograms based on other laser platforms (e.g., VISX®, Alcon's LADARVision®, Zeiss' Meditec, Nidek, Wavelight Laser Technologies, Schwind, and LaserSight, among others), nor any previous known adjustments to laser system manufacturer's preprogrammed instructions, provide the surgical outcomes according to the present invention. Thus, it should be apparent that there exists a need for such a nomogram. In particular, it would be desirable to have a nomogram, based on both lower- and higher-order aberrations information and the interactions between higher and lower order aberrations, that is directed to treating refractive errors using wavefront-guided laser ablation techniques in which the refractive error correction efficacy consistently achieves 20/20 uncorrected vision in a higher percentage of patients than previous methods.

SUMMARY AND OBJECTS OF THE INVENTION

Accordingly, it is a principal object of the present invention to provide a system and method that uses preoperative manifest refraction information, including wavefront information, to compensate for the effect of preoperative higher order aberrations on postoperative sphere and cylinder (aberration interaction) to produce a better postoperative refractive outcome compared to existing systems and methods.

It is another object of the present invention to provide a system and method for correcting refractive errors that cause myopia, hyperopia, and/or astigmatism.

It is still another object of the present invention to provide a system and method that accounts for the aberration interactions effects (e.g. coma affecting astigmatism, 3rd root mean square (RMS) affecting lower-order sphere, 3rd-order coma affecting 2d-order coma, etc.) to reduce the amount of spherical overcorrection and thereby improve postoperative refractive outcome.

Briefly described, these and other objects and features of the present invention are accomplished, as embodied and fully described herein, by a computer-implemented method for correcting refractive errors in a living eye using a laser vision correction system, which involves calculating an amount of sphere based on preoperative manifest refraction and higher order aberrations data associated with the eye, and then correcting for the calculated amount of sphere by ablating at least a portion of the eye using the laser vision correction system.

The objects and features of the invention are also accomplished, as embodied and fully described herein, by a system for correcting a refractive error in a living eye using a laser vision correction system having a first calculation subsystem for calculating an amount of sphere based on preoperative manifest refraction and higher order aberrations data associated with the eye and a correcting subsystem for ablating at least a portion of the eye based on the calculated amount of sphere. The system may include a pre-programmed instruction on a device readable medium for controlling the laser vision correction system such that the device readable medium has a memory device containing the pre-programmed instruction and wherein the pre-programmed instruction includes the amount of sphere to be corrected.

With those and other objects, features, and advantages of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

Although preferred embodiments of the invention are described for illustrative purposes, it should be understood that the invention may be embodied in other forms not specifically shown in the drawings.

Figure 1:
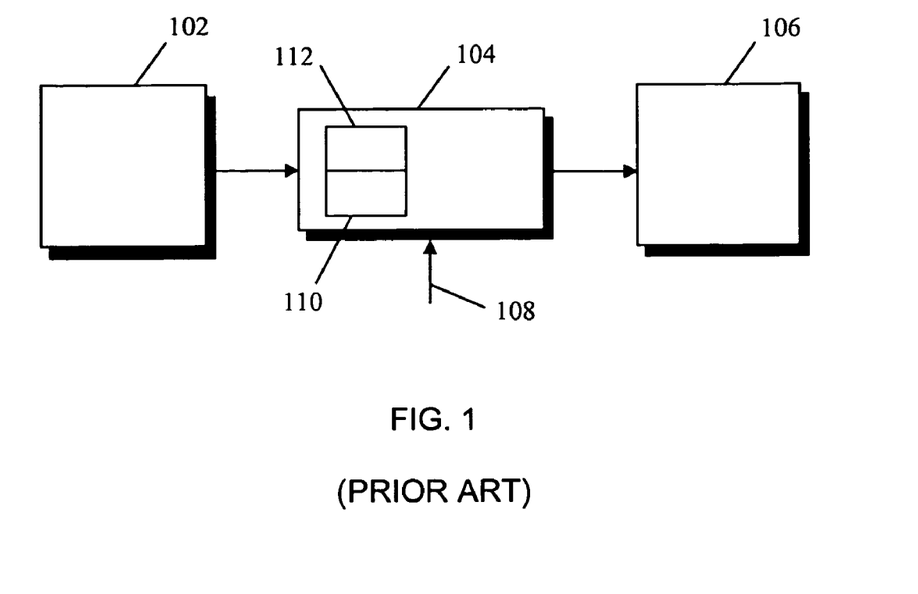
FIG. 1 is a block diagram of the major system components of a prior art laser vision correction system.

Turning first to FIG. 1, shown therein is a block diagram of the major system components of a prior art laser vision correction system. The system includes a diagnostic device 102 and a laser platform 106. The Zyoptix® system discussed above, or components thereof, is a type of laser platform 106. A control system 104, which is typically a computer, operates the laser platform 106. The control system 104 may actually be integrated into the laser platform 106.

The control system 104 utilizes software embedded on a computer-readable medium 110 that is part of the control system 104. The computer-readable medium 110 contains software for computing a laser ablation shot file 112, which is an electronic file containing information concerning the manifest refraction and wavefront sensor results, and other surgeon-entered parameters, and consists of a pulse map. The laser platform 106 includes devices for generating, directing, and steering laser energy (not shown) in response to commands executed by the control system 104 in accordance with the software. The software causes the control system 104 to manipulate the laser platform 106 and deliver the laser energy to a person's cornea.

I. Myopia

The control system 104 software includes program code containing the nomogram of the present invention for correcting refractive errors in a human eye. The nomogram of the present invention refines the existing Zylink® ablation computation software as it relates to treatment of myopia. The nomogram compensates for the effect of high order aberrations (3rd order and higher) on postoperative sphere and cylinder (a discussion of astigmatism is presented below). This allows better predictability of postoperative refractive error (i.e., sphere and cylinder) following customized LASIK treatment for myopia. The new nomogram reduces the range of postoperative refractive errors (i.e., sphere and cylinder) to within ±1 D and allows at least about 95-percent of eyes treated with the customized LASIK procedure to attain an uncorrected visual acuity (UCVA) of 20/20, or better, postoperatively.

The nomogram of the present invention compensates for the effect of preoperative higher order aberrations (3rd order and higher) on postoperative refractive error (i.e., sphere and cylinder) beyond that which is accomplished in the basic Zyoptix® system and associated Zylink® ablation computation software. A key feature of the present nomogram is the compensation of 3rd order and higher aberration terms that were found to impact the postoperative refractive outcome. Current existing algorithms/nomograms do not compensate for such interactions between higher order aberrations and lower order sphere and cylinder refractive errors.

The nomogram was derived from a statistical analysis of the preexisting data obtained from the Zyoptix® system clinical trial. A preferred embodiment of the nomogram is shown in equation (1) below:

$$\text{Sphere treatment} = 0.93 \times \{\text{preoperative manifest sphere} - 0.2376 - (0.0994 \times \text{preoperative SE}) + (0.2318 \times \text{preoperative } J0) + (0.0584 \times \text{preoperative } J45) + (0.744 \times \text{preoperative SA}) + (0.0454 \times \text{preoperative 3rd RMS})\} \quad (1)$$

In equation (1), a predicted spherical treatment parameter is based on the preoperative manifest sphere, cylinder, and axis numbers that would be included in a spectacle lens prescription, which is itself based on a diagnosis of a person's eye. The parameter SE is the spherical equivalent term as shown in equation (2) below:

$$SE = \text{sphere} + (\text{cylinder}/2) \quad (2)$$

J0 is the regular astigmatism term as shown in equation (3) below:

$$J0 = -(\text{cylinder}/2) \times \text{Cosine}(2 \times 3.142/180 \times \text{axis}) \quad (3)$$

J45 is the oblique astigmatism term as shown in equation (4) below:

$$J45 = (\text{cylinder}/2) \times \text{Sine}(2 \times 3.142/180 \times \text{axis}) \quad (4)$$

SA is the 4th-order spherical aberration term. Finally, 3rd RMS is the root mean square value of the 3rd-order aberrations (2 coma and 2 trefoil terms).

The nomogram above specifies the amount of myopic sphere to be treated based on the preoperative manifest subjective refraction (i.e., sphere, cylinder, and axis) and the preoperative high order aberrations. The subjective refraction is converted to vector format, i.e., spherical equivalent, J0 (with- and against-the-rule components), and J45 (oblique astigmatism). As equation (1) illustrates, the calculated sphere is based on the interaction between lower- and higher-order aberrations.

The nomogram above provides better treatment outcome following customized LASIK correction by compensating for the effect of higher order aberrations on postoperative sphere and cylinder. The use of the algorithm allows more patients to obtain an UCVA of 20/20 (or better), postoperatively. Further, it minimizes the need for re-treatment procedures that cost time, effort, and money and cause discomfort to the patient.

The following example illustrates the data analysis technique used to arrive at the nomogram, and in particular equation (1), of the present invention.

Example 1

Protocol

In the FDA clinical trial mentioned previously, 340 myopic eyes were treated with customized LASIK using the Zyoptix® system. The Zyoptix® system uses an algorithm that calculates the amount of sphere to be treated based on preoperative Zywave® Aberrometer refraction (i.e., sphere, cylinder, and axis) and higher order aberrations (i.e., 3rd order and higher).

In a follow up study conducted by the inventions named herein, the data for 131 of the 340 myopic eyes (i.e., 67 patients) treated with the Zyoptix® system were analyzed but the estimated postoperative spherical equivalent was modified based on the nomogram according to the present invention as set forth in the embodiment shown in equation (1).

The mean spherical equivalent of the treated eyes was $-4.94 \pm 2.02$ D (range $-1.25$ to $-10.25$ D). The maximum amount of preoperative astigmatism treated was 4.25 D. None of the eyes had prior refractive surgery or any contraindications that would otherwise exclude them from a customized LASIK procedure. Table 1 below summarizes the preoperative conditions of the treated eyes.

TABLE 1

| Parameter | 340 Eye Study (D) | 131 Eye Study (D) |
|---|---|---|
| Mean preoperative spherical equivalent | $3.66 \pm 1.52$ | $-4.94 \pm -2.02$ |
| Mean astigmatism | $-0.67 \pm 0.62$ | $-0.91 \pm -0.70$ |
| Mean preoperative HOA (0.32 μm of HOA = 0.25 D or 1 click in the phoropter) | $0.41 \pm 0.16$ | $0.53 \pm -0.19$ |

Postoperative refractive error was measured at one-month and compared to the theoretically estimated refractive outcome with the existing Zyoptix® system. A paired t-tests was used to compare differences in postoperative refractive error (i.e., spherical equivalent and sphere) between the nomogram of the present invention and the Zyoptix® system. Pearson's correlation analysis was performed to correlate the difference in manifest refraction and Zywave® PPR to postoperative spherical equivalent. Spearman's rank correlation analysis was performed to test for significant correlation between preoperative 3rd order aberration and incidence of postoperative astigmatism and also between magnitudes of astigmatism corrected and change in postoperative astigmatism axis.

Results

Figure 2:
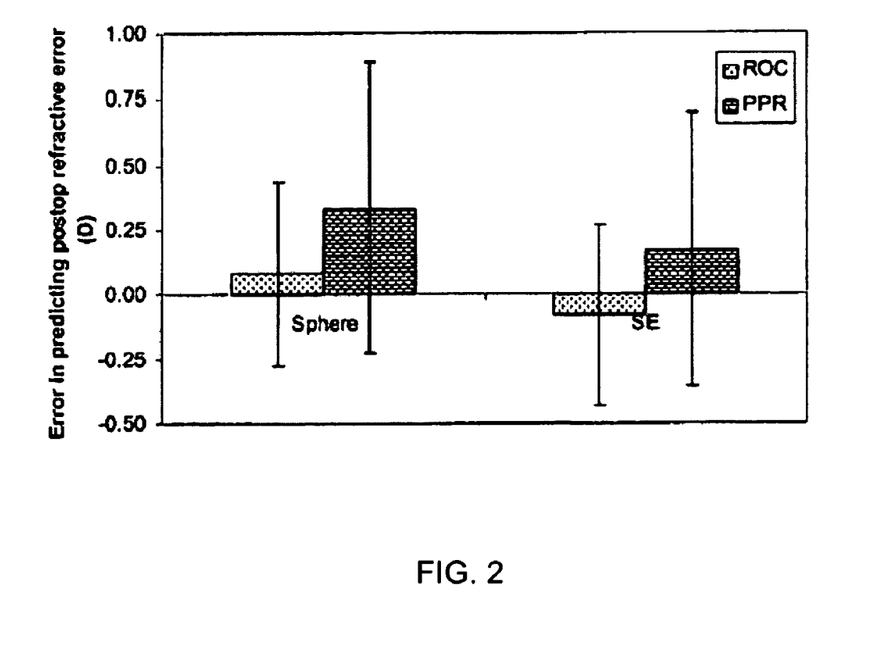
FIG. 2 is a graph comparing the error in predicting postoperative refractive error (measured in diopters, D) for sphere and spherical equivalent manifest refraction according to the nomograph of the present invention (i.e., "ROC") compared to a leading Zyoptix® system algorithm (i.e., "PPR")

The mean postoperative spherical error of the treated eyes were $0.08 \pm 0.36$ D when using customized LASIK according to the nomogram of the present invention as set forth in the embodiment shown in equation (1). That result was statistically significantly better (i.e., less hyperopic) than the mean spherical error of the patients' eyes using the Zyoptix® system without the nomogram of the present invention (i.e., $\pm 0.33 \pm 0.56$ D; t=4.30, p<0.001; as shown in FIG. 2, where "ROC" stands for "Rochester" and represents the nomogram according to equation (1)). The range of one-month postoperative sphere was $\pm 1$ D using equation (1), which was statistically significantly better than the results observed using the Zyoptix® system without the nomogram of the present invention (i.e., $-0.79$ to 2.21 D).

The mean postoperative spherical equivalents at one-month were $-0.07 \pm 0.37$ D, which was statistically significantly better than the results observed using the Zyoptix® system without the nomogram of the present invention (i.e., $\pm 0.17 \pm 0.56$ D; t=4.56, p<0.0001; as shown in FIG. 2). The nomogram of the present invention reduced the range of postoperative spherical equivalents to $\pm 1.00$ D and was statistically significantly better than the range using the Zyoptix® system ($-1.04$ to 1.81 D).

One hundred twenty of the 131 eyes (91.6-percent) had a one-month postoperative spherical equivalent of $\pm 0.5$ D, or less, and all of the eyes were within $\pm 1$ D, following treatment using equation (1). Five eyes (3.8-percent) had an over-correction or residual hyperopia (i.e., $>\pm 0.5$ D), while six other eyes (3.8-percent) had under-correction or residual myopia (i.e., $>-0.5$ D) as seen in Table 2. Following treatment using the Zyoptix® system, 90 of the 131 eyes (68.7-percent) had a postoperative refractive spherical equivalent of $\pm 0.5$ D or less. Thirty-one eyes (23.7-percent) would have obtained residual hyperopia (i.e., $>\pm 0.5$ D) and 10 eyes (7.6-percent) would have had myopia (i.e., $>-0.5$ D) postoperatively, as seen in Table 2.

TABLE 2

| 1-month SE (D) | "ROC" | B&L 93% PPR |
|---|---|---|
| <±0.25 D | 91 | 59 |
| >±0.25 D and <±0.50 D | 29 | 31 |
| >±0.50 D and <±1 D | 6 (myopia) | 8 (myopia) |
|  | 5 (hyperopia) | 21 (hyperopia) |
| >±1 D | 0 | 2 (myopia) |
|  |  | 10 (hyperopia) |

The magnitude of astigmatism correction by the Zyoptix® system was based on the PPR astigmatism estimated by a Zywave® Aberrometer. Of the eyes with postoperative astigmatism of 0.25 D or more (i.e., n=55), the rotation in the postoperative astigmatism axis was directly proportional to the magnitude of discrepancy between the manifest and the PPR astigmatism (i.e., r=0.42, p<0.001). In other words, if the PPR astigmatism was less than the manifest astigmatism (difference >0.12 D), the mean postoperative astigmatism axis was rotated by a mean of 33.44±25.96 degrees, and if the PPR astigmatism was greater than the manifest astigmatism (difference >0.12 D), the mean postoperative astigmatism axis was rotated by a mean of 58.39±34.96 degrees, relative to the preoperative astigmatism axis. However, the magnitude of the postoperative astigmatism was not significantly correlated to the magnitude of astigmatism discrepancy between manifest refraction and PPR (p>0.05).

Of the 131 eyes considered in this study, 8.4-percent of the eyes (11 total) had a spherical equivalent greater than 0.5 D but less than or equal to 1 D following treatment according to equation (1), compared to 22.1-percent of the eyes (29 total) that fell into the same range based on the PPR estimated spherical equivalents. Statistically significantly, none of the eyes had a spherical equivalent greater than 1 D following treatment according to the algorithm of the present invention, compared to 9.1-percent of the eyes (12 total) that fell into the same range based on the PPR estimated spherical equivalents.

Analysis

The laser ablation technique based on equation (1) provides better precision and reduced range of postoperative refractive outcome following customized LASIK for myopia (p<0.0001). The results demonstrated a significantly better refractive outcome in the treated eyes following treatment according to equation (1) compared to the 93-percent PPR spherical equivalent recommended used by the Zyoptix® system. In fact, there was a 30-percent reduction in the range of postoperative spherical equivalents using equation (1). 91.6-percent of the eyes had 20/20 or better uncorrected visual acuity (UCVA) and no eye had greater than 1 D error. That compares to 68.8-percent of eyes based on the 93-percent PPR. The postoperative spherical equivalent is four time less likely to be greater than 0.5 D following treatment using equation (1).

The existing Zyoptix® system provides reasonably good postoperative refractive outcome, but the incidence of postoperative refractive errors between ±0.5 to 1 D (n=29) and greater than ±1 D (n=12) is still relatively high.

The PPR estimated astigmatism was used as the magnitude of astigmatism treatment to be compliant with existing Bausch & Lomb guidelines (as per the Zyoptix® Diagnostic Workstation Operator's manual Version 1.2 A Z, Bausch & Lomb). The rotation in postoperative astigmatism axis, relative to preoperative astigmatism axis, was significantly influenced by the discrepancy in preoperative manifest astigmatism and preoperative PPR astigmatism values (r=0.42, p<0.001). In theory, when the preoperative PPR astigmatism is lower than manifest astigmatism, the laser ablation would result in relatively less astigmatism being treated (astigmatism under-correction) and hence the postoperative axis of astigmatism would not be expected to change significantly from the preoperative astigmatism axis. Likewise, if the preoperative PPR astigmatism is greater than manifest astigmatism, more laser ablation performed (astigmatism over-correction) in the corresponding meridian should result in rotation of postoperative astigmatism axis by 90°. The results of the present analysis are consistent with the above theoretical prediction as the axis rotation occurred in the expected direction. However, the magnitude of postoperative astigmatism axis rotation, relative to preoperative astigmatism axis, was different from the theoretical predictions. The postoperative rotation in astigmatism axis relative to preoperative values was 33.4±25.9° when the preoperative PPR astigmatism was less than the preoperative manifest astigmatism. When the preoperative PPR astigmatism was greater than manifest astigmatism, the mean relative rotation in postoperative astigmatism axis was 58.39±35°. The latter value is equivalent to a 31.61° rotation from preoperative, more myopic power meridian that is 90° to the preoperative astigmatism axis. The magnitude of difference between the two postoperative astigmatism axis rotations relative to preoperative axis, based on the magnitude of astigmatism treated, was significantly different (t=3.00, p<0.001). This magnitude of postoperative astigmatism axis rotation, relative to the preoperative state, could be attributed to three factors, namely, decentration in laser ablation, torsional eye movements during the procedure, and alteration of the cornea-to-lenticular astigmatism ratio from corneal ablation. The change in cornea-to-lenticular astigmatism ratio is secondary to discrepancy in the PPR and manifest astigmatism values.

A previous analysis on myopic eyes treated with customized LASIK using existing Zyoptix® algorithm, showed significant correlations between preoperative higher order aberrations and postoperative spherical equivalent. However, using the present nomogram, no significant correlation was obtained between preoperative higher order aberrations and postoperative refractive error due to the compensation of the aberration interaction effect, which is the result of correcting higher order aberrations which manifests itself in an actual correction of lower order sphere and cylinder.

Figure 3:
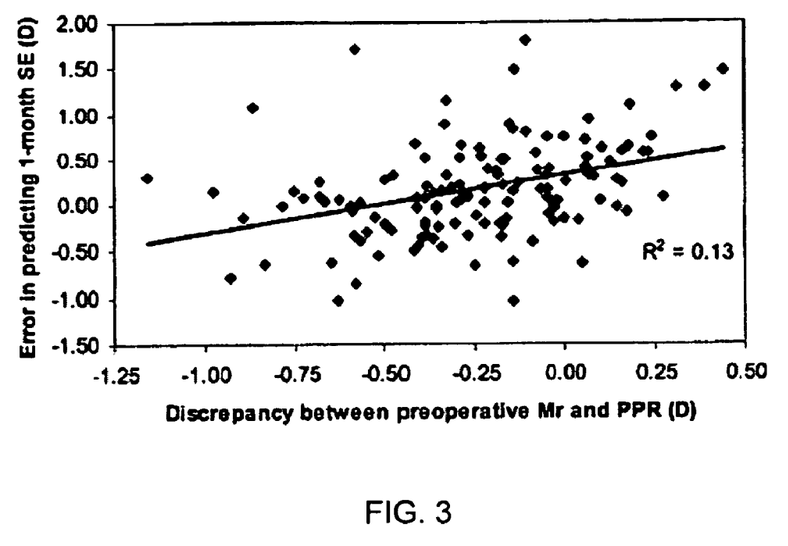
FIG. 3 is a graph showing a significant correlation between the error in predicting postoperative refractive error according to the Zyoptix® system algorithm as measured at one month (measured in spherical equivalent diopters, D) and the preoperative discrepancy between the manifest refraction and the PPR values.

The better postoperative results using the nomogram of the present invention can be attributed to two major aspects. First, the nomogram of the present invention, as represented by the embodiment of equation (1), specifies treatment based on preoperative manifest refraction while the existing Zyoptix® system algorithm recommends treatment based on an adjustment to the PPR sphere or wavefront sphere value. The Zywave® PPR measures slight less myopia than manifest refraction (mean difference in spherical equivalent is −0.25 D±0.30 D) but recommends more myopia treatment than equation (1) (mean difference in spherical equivalent is 0.26±0.40 D). A significant correlation was obtained between error in predicting postoperative refractive error by the existing Zyoptix® system algorithm and preoperative discrepancy between manifest refraction sphere and PPR sphere ($r^2$=0.13, p<0.0001, as seen in FIG. 3).

Second, the nomogram of the present invention, as represented by the embodiment of equation (1), provides a reduction in the range of postoperative refractive error (±1 D) due to the compensation of aberration interaction effect as described above. The present inventors are not aware of any published algorithms or nomograms that compensate for those aberration interaction effect. The range of postoperative refractive error (Table 2) is highly efficient considering the various surgical and biological factors that have been postulated to influence the treatment procedure and hence, postoperative changes in refraction.

Figure 4:
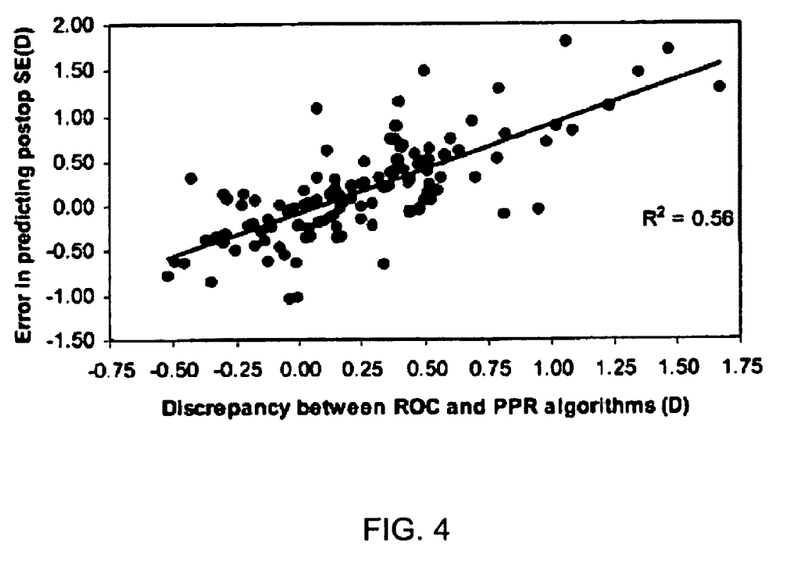
FIG. 4 is a graph showing a significant correlation between the error in predicting postoperative refractive error according to the Zyoptix® system algorithm as measured in spherical equivalents (i.e., diopters, D) and the discrepancy in the treatment magnitude recommended by the Zyoptix® system algorithm and the algorithm according to the present invention.

The recommended treatment magnitude specified by the algorithm of the present invention was significantly different than that of the existing Zyoptix® algorithm (t=7.41, p<0.0001). Further, the discrepancy in the treatment magnitude recommended by the two methods was significantly correlated to the postoperative refractive error ($r^2$=0.56, p<0.0001, as seen in FIG. 4), providing further evidence of effective treatment caused by compensation of the aberration interaction effect using the present invention.

Given the above results, it has been found that aberration interaction effect can be accounted for when using any of the available manufacturer's laser platforms to improve the outcome of the laser vision correction system being used. The aberration interaction effect may be accounted for by adjusting the laser manufacturer's preprogrammed instructions (which may or may not already account for known or predicted postoperative overcorrection or undercorrection).

Figure 5:
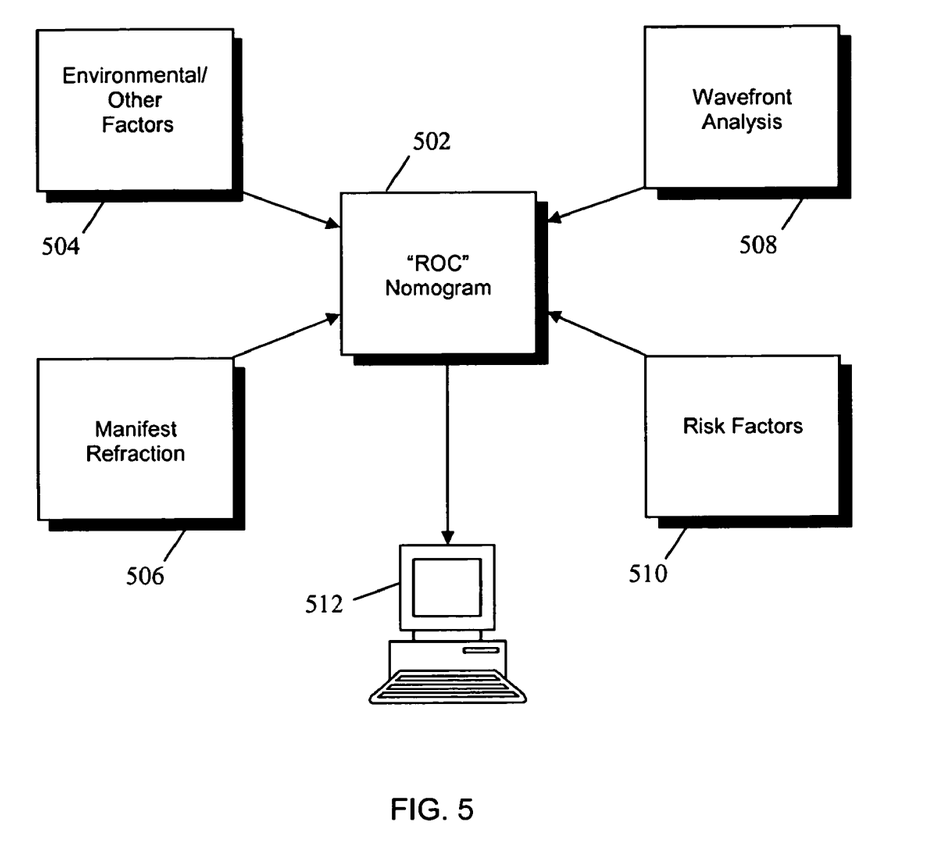
FIG. 5 is a schematic of nomograph according to the present invention showing the major inputs to the nomograph.

Turning now to FIG. 5, shown therein is a schematic of a "ROC" nomogram 502 according to the present invention. The nomogram includes the algorithm of the present invention as shown in the embodiment of equation (1). The various inputs making up parts of the nomogram 502 include the aforementioned manifest refraction data 506 and wavefront analysis data 508. The present invention provides much improved and predictable postoperative refractive outcome, but it is also limited by a multitude of factors that curb further reduction in the range of postoperative outcome. These factors can be broadly classified into a) preoperative factors such as age, repeatability of manifest refraction, repeatability and stability of wavefront aberrations; b) surgical parameters such as laser characteristics, decentration in laser ablation, and eye movements; c) postoperative factors such as corneal healing response and biomechanics, and environmental factors such as temperature and humidity. Those factors, illustrated as blocks 504 and 510 in FIG. 5, can be accounted for by modifying equation (1). A simplified modification is as follows, were each of the factors is a variable added to the equation:

$$\text{Sphere treatment}=\text{Equation (1)}+\text{var 1}+\text{var 2}+\text{var 3}+\ldots+\text{var }n \quad (5)$$

Where n is the number of variables (var) added to equation (1) (or subtracted from, multiplied by, divided into, factored out of the equation, or transformed, or applied to in some other or combination of mathematical ways). All of the information about the manifest refraction, higher order aberrations, risk factors, and surgery- or surgeon-specific information are transferred to a device readable medium, such as the memory structure of the computer 512 (or a portable device readable memory device), that may or may not be operatively connected to a laser vision correction system.

Figure 6:
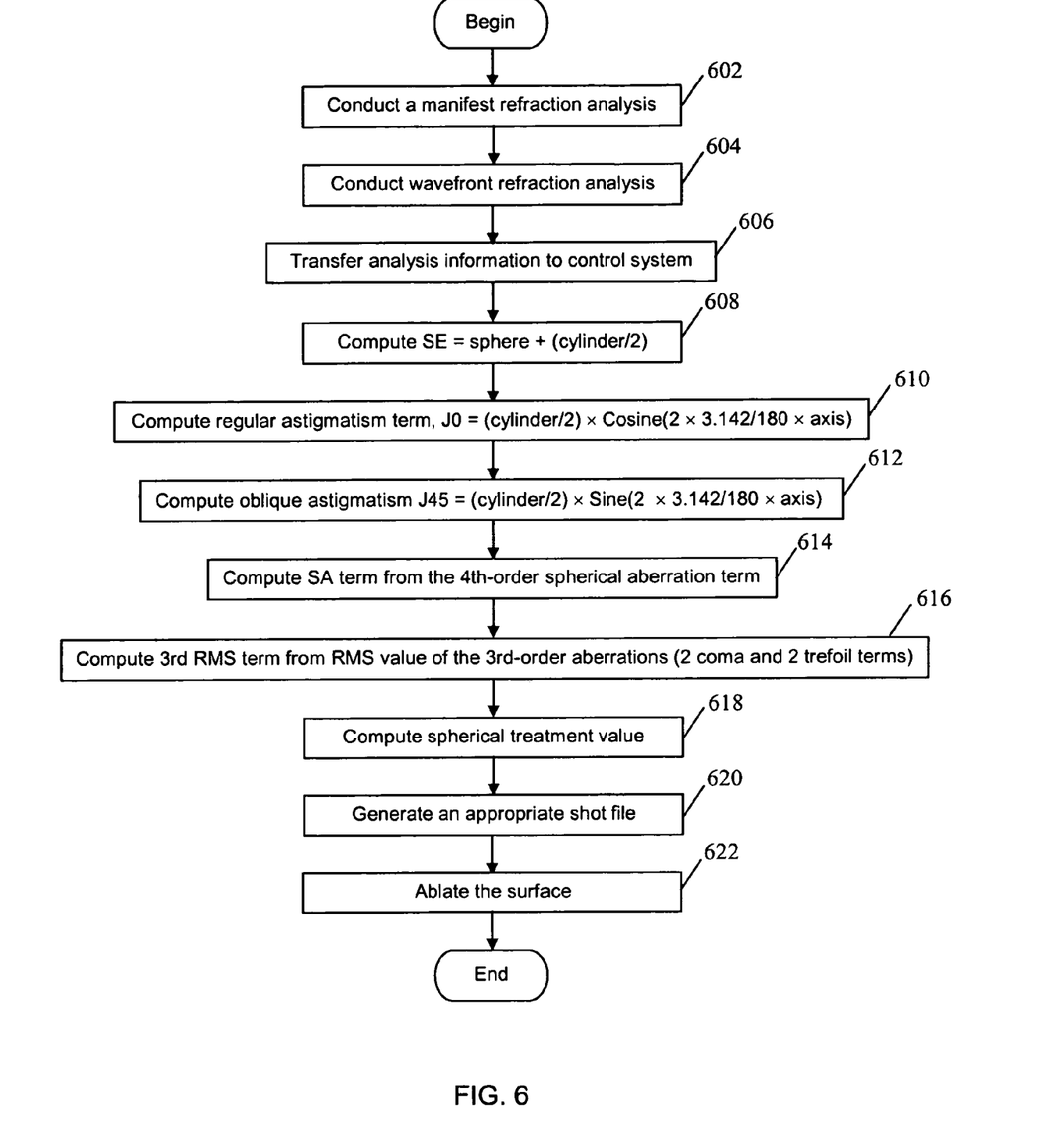
FIG. 6 is a flow chart illustrative the major steps in practicing a preferred embodiment of the present invention.

Tuning now to FIG. 6, shown therein is a flow chart of the computer implemented method of the embodiment described above. As noted previously, the first step in treating myopia is to diagnose and compute a person's predicted spherical treatment parameters, which include manifest sphere, cylinder, and axis numbers that would be included in a spectacle lens prescription. Thus, in step 602, a manifest refraction analysis is conducted of a person's eye or eyes in accordance with standard practices using well known diagnostic tools. The information obtained from the manifest refraction analysis is recorded.

Next, in step 604, a wavefront refraction analysis is conducted. The information obtained from the wavefront system is stored or otherwise recorded, preferably in an electronic form in some kind of storage medium. Steps 602 and 604 could be combined in a single step or the order of the steps could be reversed.

In step 606, the diagnostic information from the manifest refraction and wavefront analysis are input or transferred to a device readable storage medium containing programming code that includes the nomogram of the present invention. Step 606 could be completed after step 602, when the manifest refraction information is available, and it could be completed again after step 604, when the wavefront aberration information is available.

In step 608, the spherical equivalent term is computed, SE=sphere+(cylinder/2), which may be computed once the cylinder information is available.

In step 610, the regular astigmatism term is computed, J0=−(cylinder/2)×Cosine(2×3.142/180×axis). J0 may be computed once the cylinder and axis of astigmatism information are available.

In step 612, the oblique astigmatism term is computed, J45=(cylinder/2)×Sine(2×3.142/180×axis). J45 may be computed once the cylinder and axis of astigmatism information are available.

In step 614, the SA term is computed from the 4th-order spherical aberration term. SA may be computed once the wavefront information is available.

In step 616, the 3rd root mean square term is computed from the root mean square value of the 3rd-order aberrations (2 coma and 2 trefoil terms). The 3rd RMS value may be computed once the wavefront information is available.

Finally, in step 618, the final spherical treatment value is computed and transferred to the control system 104 (see FIG. 1), which allows the software of the control system 104 to generate an appropriate shot file and laser map in step 620. In step 622, the surface undergoing ablation is then ablated according to the instructions contained in the shot file and laser map.

As noted above, one of ordinary skill in the art will appreciate and understand that the computation steps 608 through 616 may be done simultaneously, in parallel, and/or sequentially in any order other than the one illustrated above.

Thus, according to the method of the present invention, the nomogram specifies the amount of sphere to be treated based on the preoperative manifest subjective refraction (i.e., sphere, cylinder, and axis) and the preoperative wavefront-diagnosed higher order aberrations. The subjective refraction is then converted to vector format, as described above, which, when embodied in the software of the customized laser treatment system, causes the laser to ablate the corneal tissue of the eyes of the person undergoing treatment.

II. Astigmatism

The presence of an increased preoperative individual 3rd order aberration (i.e., not the 3rd RMS value) and the discrepancy between the preoperative manifest refraction analysis results and the Zywave® cylinder values impact postoperative astigmatism correction outcomes. The discrepancy between the preoperative manifest refraction analysis results and the Zywave® cylinder values also impact the magnitude of the rotation in postoperative astigmatism axis relative to the preoperative axis. Thus, the nomogram of the present invention can be modified to account for this discrepancy and further enhance to efficacy and outcome of the customized laser ablation procedure. The following example illustrates the data analysis technique as it was used to arrive at a revised nomogram to further account for those discrepancies.

Example 2

Protocol 175 eyes from 89 patients treated using the nomogram according to the present invention were analyzed. Pre- and postoperative examinations included visual acuity and manifest refractions. Preoperative corneal topography was measured using an Orbscan II, by Bausch & Lomb, and the wavefront aberrations were measured using the Zywave® Aberrometer.

Results 71 of the 175 eyes (11-percent) developed significant postoperative astigmatism ($\geq 0.50$ D). The preoperative 3rd order terms and the discrepancy between the preoperative manifest refraction analysis information and the preoperative Zywave® cylinder information obtained from the eyes were compared; the results are shown on Table 3 (bold values indicate statistical significance).

TABLE 3

| Postop cyl | Preop $3^{rd}$ RMS (µm) | Preop V trefoil (µm) | Preop V coma (µm) | Preop H coma (µm) | Preop H trefoil (µm) | Preop discrepancy in cyl (D) |
|---|---|---|---|---|---|---|
| $\geq 0.50$ D | 0.26 ± 0.43 | −0.11 ± 0.14 | −0.20 ± 0.23 | −0.06 ± 0.18 | 0 ± 0.10 | 0.04 ± 0.23 |
| <0.50 D | 0.40 ± 0.17 | 0.12 ± 0.33 | −0.04 ± 0.22 | −0.15 ± 0.26 | −0.04 ± 0.20 | −0.12 ± 0.25 |
| t-Test | 3.00 | 5.66 | 2.89 | −1.96 | −1.24 | −2.81 |

The two groups above (eyes with postoperative cylinder $\geq 0.50$ and eyes with postoperative cylinder <0.50 D) did not have any significant difference in preoperative astigmatism (i.e., −0.91±0.75 D and −0.81±0.70 D, respectively).

The eyes that did not develop significant postoperative astigmatism had lower preoperative 3rd RMS values (i.e., 0.26±0.43 D) than the eyes that developed significant postoperative astigmatism (i.e., 0.40±0.17 D). The eyes with significant postoperative astigmatism had greater V. Coma (i.e., −0.20±0.23 D) than the eyes that did not develop significant astigmatism (i.e., −0.04±0.22 D). The eyes that developed significant postoperative astigmatism had equal but opposite sign in preoperative V. Trefoil (i.e., −0.11±0.14 D) than those that did not develop significant postoperative astigmatism (0.12±0.33 D). Eyes with significant postoperative astigmatism had low preoperative discrepancy between the preoperative manifest refraction astigmatism and preoperative Zywave® astigmatism values (i.e., 0.04±0.23 D) compared to eyes that did not develop postoperative astigmatism (i.e., −0.12±0.25 D).

Analysis

The nomogram containing the algorithm of the present invention is able to compensate well for the preoperative 3rd RMS values, but these eyes need further refinement because they have greater preoperative vertical coma (and maybe V. trefoil). These eyes tended to develop greater postoperative astigmatism.

Among eyes with high postoperative astigmatism, the treatment of vertical coma combined with decentration changes the axis of astigmatism and coma resulting in postoperative manifest astigmatism.

The magnitude of astigmatism correction by the Zyoptix® software is based on the preoperative PPR astigmatism estimated by the Zywave® Aberrometer. Among eyes with postoperative astigmatism of 0.50 D or more (n=71), the rotation in the postoperative astigmatism axis was directly proportional to the magnitude of the discrepancy between the preoperative manifest astigmatism and the preoperative PPR astigmatism (i.e., r=0.29, p<0.001). In other words, if the preoperative astigmatism treated was less than the preoperative manifest astigmatism (difference >0.12 D), the postoperative astigmatism axis was rotated by 28.28±20.70-degrees, and if the preoperative wavefront astigmatism treated was greater than the preoperative manifest astigmatism (difference >0.12 D), the postoperative astigmatism axis was rotated by 49.21±26.87-degrees, relative to the preoperative astigmatism axis. The difference in the magnitude of axis rotation was found to be statistically significant (i.e., t=3.10, p<0.001). However, the magnitude of postoperative astigmatism was not significantly correlated to the magnitude of the astigmatism discrepancy between preoperative manifest refraction and preoperative PPR (p>0.05).

Table 4 identifies what are believed to be the relationships between the preoperative cylinder discrepancy and the vertical coma on postoperative cylinder.

TABLE 4

| Preoperative Cylinder Discrepancy | Preoperative Vertical Coma | Postoperative Cylinder |
|---|---|---|
| High | Low | High |
| High | High | Low |
| Low | Low | Low |
| Low | High | High |

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A computer-implemented system for improving the outcome of laser vision correction treatments of living eyes, each of the eyes characterized by a value representing each of a preoperative sphere, cylinder, axis, and higher-order aberrations, comprising:
   a processor; a first subsystem for receiving or calculating an amount of treatment sphere and for controlling a laser vision correction device, the treatment sphere amount being derived from:
      preoperative subjective refraction data, including the sphere, cylinder, and axis values
      an amount of a secondary sphere adjustment derived from preoperative wavefront data measured using wavefront sensors or different types of aberrometers including topography devices, the wavefront data including the higher-order aberrations values,
      a calculated preoperative spherical equivalent amount based on the preoperative subjective sphere and cylinder values, a calculated preoperative with or against the rule astigmatism amount based on the preoperative subjective cylinder and axis values, a calculated preoperative oblique astigmatism amount based on the preoperative subjective cylinder and axis values, a calculated preoperative 4th-order spherical aberration amount based on the preoperative wavefront data, and a calculated 3rd order root mean square amount based on the amount of preoperative wavefront 3rd order coma and trefoil data to be corrected.

2. The system of claim 1, further comprising:

a second subsystem for calculating an amount of astigmatism based on preoperative manifest refraction and preoperative higher order aberrations data.

3. The system of claim 1, wherein the preoperative manifest refraction data comprises at least the preoperative manifest sphere amount, the preoperative spherical equivalent amount, the with or against the rule astigmatism amount (J0), and the oblique astigmatism amount (J45).

4. The system of claim 1, wherein the preoperative higher-order aberrations data comprises at least the 4th-order spherical aberration and the 3rd root mean square amount, and optionally other higher order aberration amounts.

5. The system of claim 1, further comprising a second subsystem for adjusting the calculated treatment sphere amount based on at least one preoperative risk or other factor.

6. The system of claim 5, wherein the at least one preoperative risk factor is selected from the group consisting of a combination comprising a high preoperative Coma and a low preoperative Δcylinder value, a combination comprising a high preoperative Δcylinder and a low preoperative Coma value, a combination comprising a preoperative wavefront cylinder being greater than a preoperative manifest cylinder value, a combination comprising of a preoperative wavefront cylinder being less than a preoperative manifest cylinder value, and an age of the eye.

7. The system of claim 5, wherein the at least one other factors is selected from the group consisting of a repeatability of the manifest refraction data, a repeatability and stability of a wavefront aberration, a predicted corneal healing response, and a biomechanical structure of the eye.

8. The system of claim 1, wherein the treatment sphere amount is calculated using equation (1):

$$0.93 \times \{\text{preoperative manifest sphere} - 0.2376 - (0.0994 \times \text{preoperative SE}) + (0.2318 \times \text{preoperative } J0) + (0.0584 \times \text{preoperative } J45) + (0.744 \times \text{preoperative SA}) + (0.0454 \times \text{preoperative 3rd RMS})\} \quad (1)$$

* * * * *